(12) United States Patent
Mishra

(10) Patent No.: US 7,462,268 B2
(45) Date of Patent: Dec. 9, 2008

(54) PARTICLE/CELL SEPARATION DEVICE AND COMPOSITIONS

(76) Inventor: Allan Mishra, 340 August Cir., Menlo Park, CA (US) 94025

( * ) Notice: Subject to any disclaimer, the term of this patent is extended or adjusted under 35 U.S.C. 154(b) by 225 days.

(21) Appl. No.: 11/205,283

(22) Filed: Aug. 16, 2005

(65) Prior Publication Data

US 2006/0127382 A1 Jun. 15, 2006

Related U.S. Application Data

(60) Provisional application No. 60/603,249, filed on Aug. 20, 2004.

(51) Int. Cl.
*C02F 1/40* (2006.01)
(52) U.S. Cl. .................... 204/600; 435/2; 435/283.1
(58) Field of Classification Search .................. None
See application file for complete search history.

(56) References Cited

U.S. PATENT DOCUMENTS

| | | | |
|---|---|---|---|
| 4,081,331 A * | 3/1978 | Weiss .................... 202/181 |
| 4,663,289 A | 5/1987 | Veech |
| 4,931,395 A | 6/1990 | Griffin |
| 5,079,236 A | 1/1992 | Drizen et al. |
| 5,124,316 A | 6/1992 | Antoniades et al. |
| 5,147,776 A | 9/1992 | Koerner, Jr. |
| 5,165,938 A | 11/1992 | Knighton |
| 5,178,883 A | 1/1993 | Knighton |
| 5,269,290 A | 12/1993 | Barrett et al. |
| 5,336,387 A * | 8/1994 | Egen et al. .................. 204/627 |
| 5,385,937 A | 1/1995 | Stamler et al. |
| 5,403,272 A | 4/1995 | Deniega et al. |
| 5,449,688 A | 9/1995 | Wahl et al. |
| 5,474,891 A | 12/1995 | Murphy |
| 5,494,590 A | 2/1996 | Smith et al. |
| 5,510,102 A | 4/1996 | Cochrum |
| 5,578,460 A * | 11/1996 | Ebersole et al. ............... 435/29 |
| 5,578,565 A | 11/1996 | Chao et al. |
| 5,585,007 A | 12/1996 | Antanavich et al. |
| 5,599,558 A | 2/1997 | Gordinier et al. |
| 5,614,204 A | 3/1997 | Cochrum |
| 5,643,786 A | 7/1997 | Cohen et al. |
| 5,788,662 A | 8/1998 | Antanavich et al. |
| 5,834,418 A | 11/1998 | Brazeau et al. |
| 5,905,142 A | 5/1999 | Murray |
| 5,935,850 A | 8/1999 | Clark et al. |
| 6,063,297 A | 5/2000 | Antanavich et al. |
| 6,098,631 A | 8/2000 | Holoshitz et al. |
| 6,132,396 A | 10/2000 | Antanavich et al. |
| 6,183,442 B1 | 2/2001 | Athanasiou et al. |
| 6,214,338 B1 | 4/2001 | Antanavich et al. |
| 6,242,594 B1 | 6/2001 | Kelly |
| 6,280,473 B1 | 8/2001 | Lemperle et al. |
| 6,315,992 B1 | 11/2001 | Noh et al. |
| 6,322,785 B1 | 11/2001 | Landeberg et al. |
| 6,432,119 B1 | 8/2002 | Saadat |
| 6,454,804 B1 | 9/2002 | Ferree |
| 6,712,851 B1 | 3/2004 | Lemperle et al. |
| 6,811,777 B2 | 11/2004 | Mishra |
| 2001/0031978 A1 | 10/2001 | Kipke et al. |
| 2002/0006437 A1 | 1/2002 | Grooms et al. |
| 2002/0032155 A1 | 3/2002 | Ferree |
| 2002/0058030 A1 | 5/2002 | Monroy et al. |
| 2002/0082220 A1 | 6/2002 | Hoemann et al. |
| 2003/0116512 A1 | 6/2003 | Delbert Antwiller et al. |
| 2003/0152639 A1 | 8/2003 | Britton et al. |
| 2003/0185812 A1 | 10/2003 | Ferree |
| 2003/0192554 A1 | 10/2003 | Ferree |
| 2003/0236573 A1 | 12/2003 | Evans et al. |
| 2004/0126885 A1 | 7/2004 | Cines et al |
| 2004/0220101 A1 | 11/2004 | Ferree |
| 2004/0220102 A1 | 11/2004 | Ferree |
| 2004/0244806 A1 | 12/2004 | Ferree |
| 2005/0043738 A1 | 2/2005 | Ryan |
| 2005/0064042 A1 | 3/2005 | Vunjak-Novakovic et al. |
| 2005/0186193 A1 | 8/2005 | Mishra |
| 2006/0029578 A1 | 2/2006 | Hoemann et al |
| 2006/0041243 A1 | 2/2006 | Nayak et al |
| 2006/0127382 A1 | 6/2006 | Mishra |
| 2006/0235306 A1 | 10/2006 | Cotter et al. |
| 2006/0263407 A1 | 11/2006 | Mishra |
| 2007/0014784 A1 | 1/2007 | Nayak et al |
| 2007/0037737 A1 | 2/2007 | Hoemann et al. |
| 2007/0042016 A1 | 2/2007 | Nayak et al. |
| 2007/0110737 A1 | 5/2007 | Mishra |
| 2007/0122906 A1 | 5/2007 | Mishra |

FOREIGN PATENT DOCUMENTS

| | | |
|---|---|---|
| EP | 0 142 339 | 5/1985 |
| EP | 0 417 818 | 3/1991 |
| WO | WO 00/01427 | 1/2000 |
| WO | WO 03/015800 | 2/2003 |
| WO | WO 2004/022078 | 3/2004 |
| WO | WO 2005/065242 | 7/2005 |

OTHER PUBLICATIONS

U.S. Appl. No. 10/176,272, filed Mar. 21, 2003, Dorian et al.

(Continued)

*Primary Examiner*—Sandra Saucier
*Assistant Examiner*—Satyendra K Singh
(74) *Attorney, Agent, or Firm*—Knobbe, Martens, Olson & Bear, LLP

(57) ABSTRACT

A particle/cell separation device is described which is particularly adapted for neutrophil depletion from a preparation of whole blood or platelet-rich plasma. Also described are blood and platelet rich plasma compositions produced using the device which are neutrophil-depleted.

4 Claims, 7 Drawing Sheets

OTHER PUBLICATIONS

U.S. Appl. No. 10/394,801, filed Mar. 21, 2003, Dorian et al.

U.S. Appl. No. 10/394,828, filed Mar. 21, 2003, Dorian et al.

Edwards, et al. "Autologous Blood Injections for Refractory Lateral Epicondylitis," *The Journal of Hand Surgery*, pp. 272-278, vol. 28A, No. 2, Mar. 2003.

Gruber, et al. "Platelets Stimulate Proliferation of Bone Cells: Involvement of Platelet-Derived Growth Factor, Microparticles and Membranes," *Clin. Oral Impl. Res*, vol. 13, pp. 529-535, 2002.

Kahn, et al., "Overuse Tendinosis, Not Tendinitis, Part 1: A New Paradigm for a Difficult Clinical Problem," *The Physician and Sportsmedicine*, vol. 28, No. 5, 8 pages, May 2000.

Kahn, et al. "Overuse Tendinosis, Not Tendinitis, Part 2: Applying the New Approach to Patellar Tendinopathy," *The Physician and Sportsmedicine*, vol. 28, No. 6, 12 pages, Jun. 2000.

Khan, et al. "Histopathology of Common Tendinopathies: Update and Implications for Clinical Management," *Clinical Sports Medicine*, vol. 27, No. 6, 1999.

Marx, et al. "Platelet-rich Plasma—Growth Factor Enhancement for Bone Grafts," *Oral Surgery Oral Medicine Oral Pathology*, vol. 85, No. 6, pp. 638-646, Jun. 1998.

Price, et al. "Local Injection Treatment of Tennis Elbow—Hydrocortisone, Triamcinolone and Lignocaine Compared," *British Journal of Rheumatology*, vol. 30, pp. 39-44, 1991.

Cohen, et al. in *Principles of Surgery*, Chapter 8, "Wound Care and Wound Healing," pp. 263-295, (Seymore, et al. Editors), New York, 1999.

Coller, et al. "The pH Dependence of Quantitative Ristocetin-Induced Platelet Aggregation: Theoretical and Practical Implications—A New Device for Maintenance of Platelet-Rich Plasma pH," *Blood*, vol. 47, No. 5, pp. 841-854, May 1976.

Snyder, et al. "Calcium-Dependent Proteolysis of Actin During Storage of Platelet Concentrates," *Blood*, vol. 73, No. 5, pp. 1380-1385, 1989.

Tang, et al. "The Effects of pCO2 and pH on Platelet Shape Change and Aggregation for Human and Rabbit Platelet-Rich Plasma," *Thrombosis Research*, vol. 10, No. 1, pp. 135-145, 1977.

Taylor, et al. "The Response of Rabbit Patellar Tendons After Autologous Blood Injection," *Medicine & Science in Sports & Exercise*, vol. 34, No. 1, pp. 70-73, 2001.

Harvest Technologies GmbH Brochure for SmartPReP 2, 2002.

Website download from Medtronic, "Magellan" System Features and Benefits, 3 pages, 2004.

Cell Factor Technologies, Inc., Brochure for GPS II Platelet Concentrate System, 10 pages, 2004.

Cell Factor Technologies, Inc., Brochure for Boost Demineralizedbonematrix, 6 pages, 2004.

DePuy AcroMed, Inc. Brochure for Symphony Platelet Concentrate System, 10 pages, 2001.

Yang, et al. "Dielectric Properties of Human Leukocyte Subpopulations Determined by Electrorotation as a Cell Separation Criterion," *Biophysical Journal*, vol. 76, pp. 3307-3314, Jun. 1999.

International Search Report dated Mar. 21, 2006.

Feuerstein, et al. "Congestive Heart Failure and Genomic Medicine: A Look into the 21$^{st}$ Century," *Cardiovascular Drugs and Therapy*, vol. 11, No. 6, 713-717, 1997.

Knebel, et al. "Heart Failure: State of the Art Treatment and Options," *Clinical Nephrology*, vol. 60, Suppl. 1, pp. S59-S66, 2003.

McCarthy, "New Surgical Options for the Failing Heart," *Journal of Heart Valve Disease*, vol. 8, No. 5, pp. 472-475, 1999.

Shim, et al. "Stem Cell Cardiomyoplasty: State of the Art," *Annals of the Academy of Medicine, Singapore*, vol. 33, No. 4, pp. 451-460, 2004.

Barrett, et al. "Growth Factors for Chronic Plantar Fasciitis?" *Podiatry Today*, pp. 37-42, Nov. 2004.

Eppley, et al. "Platelet Quantification and Growth Factor Analysis from Platelet-Rich Plasma: Implications for Wound Healing," *Plastic and Reconstructive Surgery*, pp. 1502-1508, vol. 114, No. 6, Nov. 2004.

Floryan, et al. "Home Study Program: Intraoperative Use of Autologous Platelet-Rich and Platelet-Poor Plasma for Orthopedic Surgery Patients," *Aorn Journal*, vol. 80, No. 4, pp. 667-678, Oct. 2004.

Balk, et al. "Outcome of Surgery for Lateral Epicondylitis (Tennis Elbow): Effect of Worker's Compensation," *The American Journal of Orthopedics*, pp. 122-126, Mar. 2005.

Martinez-Gonzalez, et al. "Do Ambulatory-Use Platelet-Rich Plasma (PRP) Concentrates Present Risks," *Medicina Oral*, vol. 7, pp. 375-390, 2002.

Cotter, et al. "A Novel Method for Isolation of Neutrophils from Murine Blood Using Negative Immunomagnetic Separation," *The American Journal of Pathology*, vol. 159, pp. 473-481, 2001.

\* cited by examiner

Technical Specifications/Neutrophil Separation Device

Intravenous tubing attached to a network of 12-15 micron "A" cells.
The cells could be constructed of medical grade plastic tubing or silicon tubing. The cells should have a tight radius of curvature.

Descriptive Example 1

Syringe containing platelet rich plasma (also containing many neutrophils)

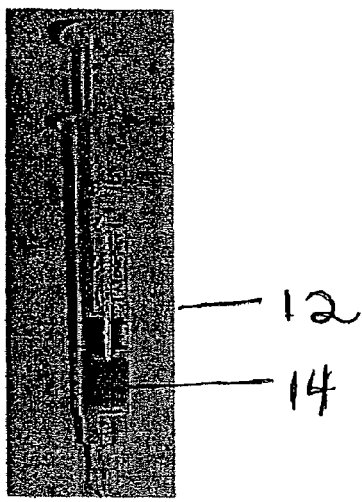

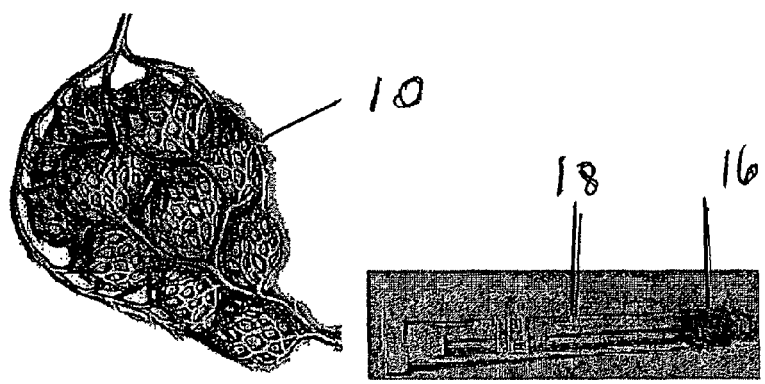

Neutrophils get filtered out by the device and are not present in blood collection tube

Figure 2

EXAMPLE 1

EXAMPLE 2

EXAMPLE 3

PARTICLE/CELL SEPARATION DEVICE AND COMPOSITIONS

RELATED APPLICATIONS

This application claim priority to U.S. Application No. 60/603,249 filed Aug. 20, 2004 which is incorporated herein by reference.

BACK GROUND OF THE INVENTION

1. Field of the Invention

In one embodiment, the invention relates to a particle or cell separation device that separates specific cell types such as neutrophils or stem cells or particles from bodily fluids such as platelets and other blood products such as red cells and plasma. Also encompassed are the bodily fluids which have been processed through the disclosed device, particularly compositions which are enriched in platelets and depleted in neutrophils.

2. Description of the Related Art

Several devices are now on the market that can process a small amount of peripheral blood (20-60 cc) automatically or semiautomatically into a fraction of that plasma that is rich in platelets. The material obtained from these devices is known as platelet rich plasma or platelet concentrate. This material is being used to augment bone grafting or to initiate soft tissue healing (See U.S. Pat. No. 6,811,777, which is incorporated herein by reference). The basis of this healing is likely due to the high concentration of growth factors found with platelets. It has been established, however, that some of the cells in platelet rich plasma may adversely affect healing or even cause further damage (Iba et al Circulation October 2002). Specifically, the neutrophils (a type of white blood cell also known as polymorphonuclear cells) contain a variety of powerful enzymes that can cause tissue inflammation. These may be present at levels of $1-3 \times 10^9$ per unit of whole blood and it is postulated by the inventor that removal of the neutrophils from the platelet rich plasma or whole blood may have significant value.

Importantly, neutrophils are also considered to be harmful in blood transfusions. Several devices already exist that attempt to filter or reduce the concentration of neutrophils prior to transfusions. Further, during cardiovascular bypass surgery when a patient's blood is pumped via a machine for a period of time, the perfusionist may attempt to filter out the neutrophils. Some evidence suggests that there is a better survival rate for patients that have these cells removed during the procedure. The reason for the increased survival is a lower rate of pulmonary complications after surgery. Presently, however, these filters only work incompletely and are not functional for small volumes of blood. A recent experiment involving platelet rich plasma revealed a 96% reduction in total platelet concentration when using a commercially available neutrophil reduction filter. Sixty percent of the volume (3 out of 5 cc) was also trapped in the filter (Mishra, data on file 2003). Clearly, this filter would not be helpful for specifically reducing neutrophils in platelet rich plasma. What is needed is a device that is effective in separating out neutrophils for both small and large volumes of blood while maintaining the platelet concentration. Presently, this device does not exist. Also, no available device mimics the body's own ability to filter neutrophils. This leads to the concept behind a new physiologic neutrophil separation device.

SUMMARY OF THE INVENTION

In one embodiment, the present invention is directed to a cell separation device which includes an inlet end portion including an inlet port for receiving a fluid sample; an outlet end portion including at least one collection port for removing separated components of the fluid sample; and a flow path comprising a tubular material in fluid communication with the inlet end portion and the outlet end portion. Preferably, the tubular material is latticed or coiled and is made of plastic or silicon.

In a preferred embodiment, the flow path is placed within an electric field. Preferably, the tubular material is charged. In some embodiments, the outlet end has a positive charge and the inlet end has a negative charge.

In some embodiments, the cell separation device is part of a larger system that includes a blood filtering device. Preferably, the blood filtering device is adapted for platelet enrichment such as production of platelet rich plasma.

Also encompassed within the scope of the invention are compositions produced by the described device. Preferably, compositions produced by the device have a reduced neutrophil content. In a preferred embodiment, the composition includes whole blood or platelet rich plasma in which the neutrophil content has been reduced by 10% or more. Preferably, the composition is neutrophil-depleted whole blood or platelet rich plasma, wherein a neutrophil content has been reduced by at least 5% compared to a starting material. More preferably, the neutrophil content in the neutrophil-depleted whole blood or platelet rich plasma has been reduced by at least 10% compared to a starting material.

In one embodiment, the invention is directed to a device for separation of neutrophils from platelet rich plasma including an inlet end portion including an inlet port for receiving a sample of platelet rich plasma; an outlet end portion including at least one collection port for removing neutrophil-depleted platelet rich plasma; and a flow path which includes a tubular material in fluid communication with the inlet end portion and the outlet end portion. Preferably, the tubular material is latticed or coiled.

In one embodiment, the invention is directed to a method of preparing neutrophil-depleted platelet rich plasma including the steps of obtaining a blood sample from a patient; obtaining platelet rich plasma from the blood sample; passing the platelet rich plasma through the cell separation device described above to obtain neutrophil-depleted platelet rich plasma; and collecting the neutrophil-depleted platelet rich plasma.

In an alternate embodiment, the invention is directed to a method of preparing neutrophil-depleted platelet rich plasma including the steps of obtaining a blood sample from a patient; passing the blood sample through the cell separation device described above to obtain neutrophil-depleted blood; and processing the neutrophil-depleted blood to obtain neutrophil-depleted platelet rich plasma.

Embodiments of the invention are directed to methods of treating an injured tissue in an individual which include at least one of the steps of determining a site of tissue injury in the individual; and introducing a neutrophil-depleted platelet-rich plasma composition into and around the site of tissue injury. In preferred embodiments, the tissue is connective tissue, cardiac muscle, skeletal muscle, disc material, a vertebral body, brain, spinal cord, or vascular tissue. In a more preferred embodiment of the invention, the tissue is a connective tissue.

Preferred embodiments of the invention include the step of titrating the neutrophil-depleted platelet-rich plasma to obtain a pH of about 7.3 to 7.5. Preferably, the titration is performed using a bicarbonate buffer.

In preferred embodiments, the neutrophil-depleted platelet-rich plasma composition includes platelets obtained from the individual.

In some preferred embodiments, no exogenous activator is added to the composition prior to its introduction into and around the site of injury.

In some preferred embodiments, one or more ingredients selected from thrombin, epinephrine, collagen, calcium salts, and pH adjusting agents is mixed into the neutrophil-depleted platelet composition substantially simultaneously with the introduction into and around the site of tissue injury, .

Embodiments of the invention are directed to a neutrophil-depleted platelet-rich plasma composition for the treatment of an injured tissue which includes neutrophil-depleted platelet-rich plasma; and a pH adjusting agent. Preferably, the neutrophil-depleted platelet-rich plasma composition does not contain an activator of the neutrophil-depleted platelet-rich plasma. Preferably, the pH adjusting agent provides a pH of about 7.3 to 7.5. Preferably, the pH adjusting agent is a bicarbonate buffer. In preferred embodiments, the plasma used for the neutrophil-depleted platelet-rich plasma is from an autologous source.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIG. 2 shows the tubing network of FIG. 1 coupled to a syringe containing platelet rich plasma and a collecting tube to collect the platelet rich plasma from which neutrophils have been filtered out.

DETAILED DESCRIPTION OF THE PREFERRED EMBODIMENT

In the human pulmonary vasculature, tightly coiled loops of blood vessels exist that are quite narrow (10 to 30 microns in diameter). Neutrophils are between 12 and 15 microns in diameter. Red blood cells by comparison are 7-8 microns in diameter and platelets are much smaller than red cells. Therefore, during circulation in these loops, some neutrophils get stuck and this can lead to significant inflammation and damage of the lung tissue. This is the problem that is partially solved by filtering out the neutrophils during cardiopulmonary bypass.

Neutrophils, as stated above, are a type of white blood cell found commonly in whole blood. They are attracted to dyes that do not have a positive or negative charge. Therefore, they are neutral. Platelets and other white blood cells such as monocytes and lymphocytes, conversely, have a negative surface membrane charge. Importantly, also, neutrophils are less deformable than red blood cells (also known as erythrocytes). Because the neutrophils are less capable of changing shape and are relatively large, they take longer to pass through either a tight radius of curvature or through an area of constriction within a blood vessel. This partially explains why neutrophils can get stuck in the tight pulmonary circulation and cause lung damage.

In the disclosed device, separation is on the basis of size, shape and charge. Neutrophils are larger, less deformable and neutrally charged relative to other blood components which are smaller, deformable and negatively charged. Thus, by forcing a blood, platelet or platelet rich plasma fraction through a narrow, twisted and/or charged environment, neutrophils are preferentially removed from other blood components.

The disclosed device is useful for separation of cells, particles and proteins from an aqueous sample. Preferably, the aqueous sample is a body fluid such as whole blood, serum, plasma, or platelet rich plasma. Preferably, the device is adapted for separation of neutrophils or stem cells.

In one embodiment, tubing is coiled, latticed, and/or twisted to mimic the pulmonary vasculature. The tubing may be made of any appropriate material as discussed below. The tubing mimics the pulmonary circulation in size and form.

Figure 1:
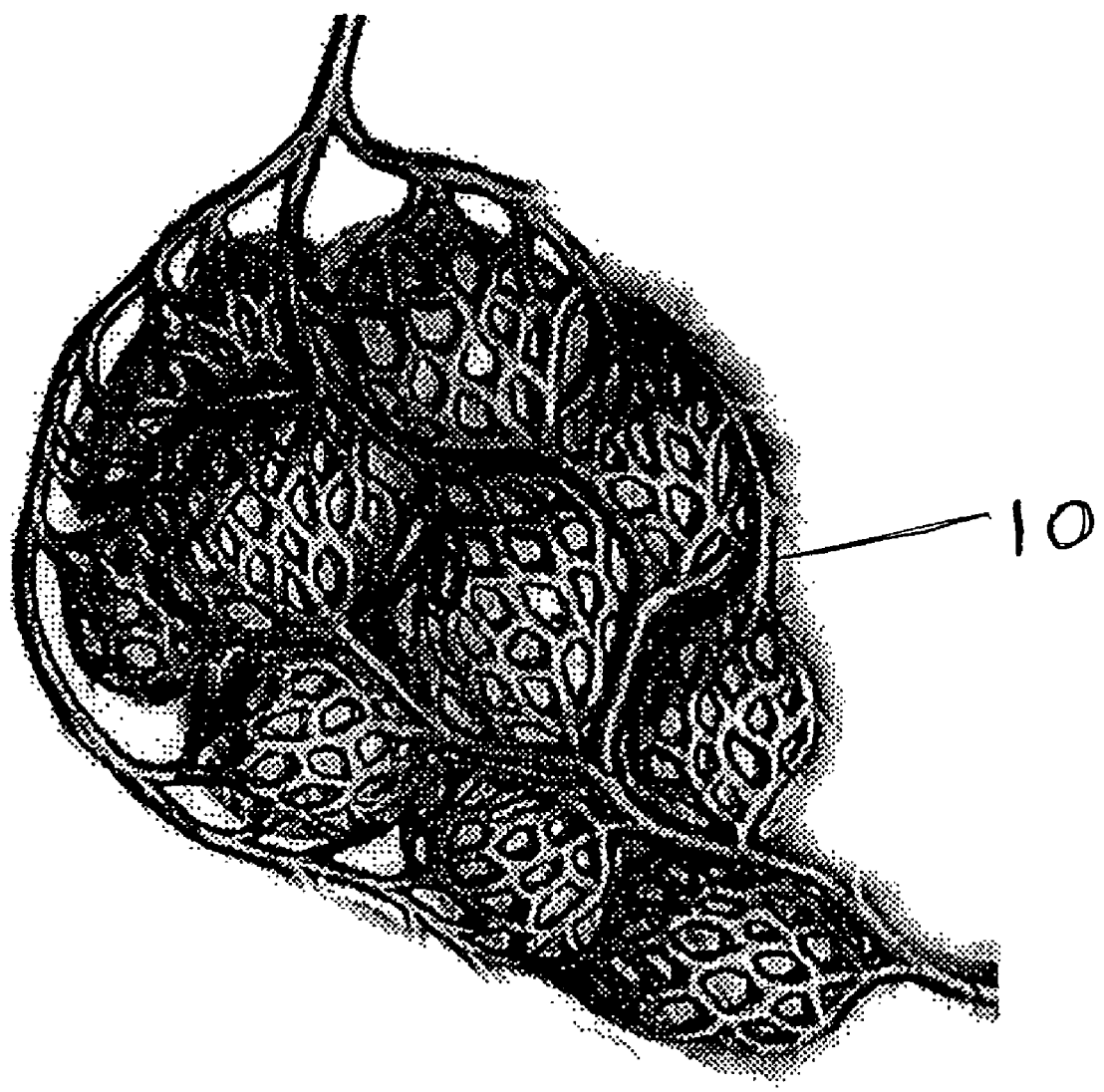
FIG. 1 shows intravenous tubing attached to a network of 12-15 micron "A" cells. The cells could be constructed of medical grade plastic tubing or silicon tubing. The cells should have a tight radius of curvature.

One embodiment of a cell separation device of the invention is shown in FIG. 1 which shows a latticed arrangement 10, similar to the pulmonary vasculature. FIG. 2 shows how the device is coupled to a syringe 12 containing platelet rich plasma 14. The treated platelet rich plasma with reduced neutrophil content 16 is then collected in a collecting tube 18.

In a preferred embodiment, this design of FIG. 1 is placed within an electrical field or the tubing is charged. The tight coiling and electrical field functions to separate different types of cells and/or particles that are found within aqueous samples such as whole blood or plasma.

Figures 3, 4:
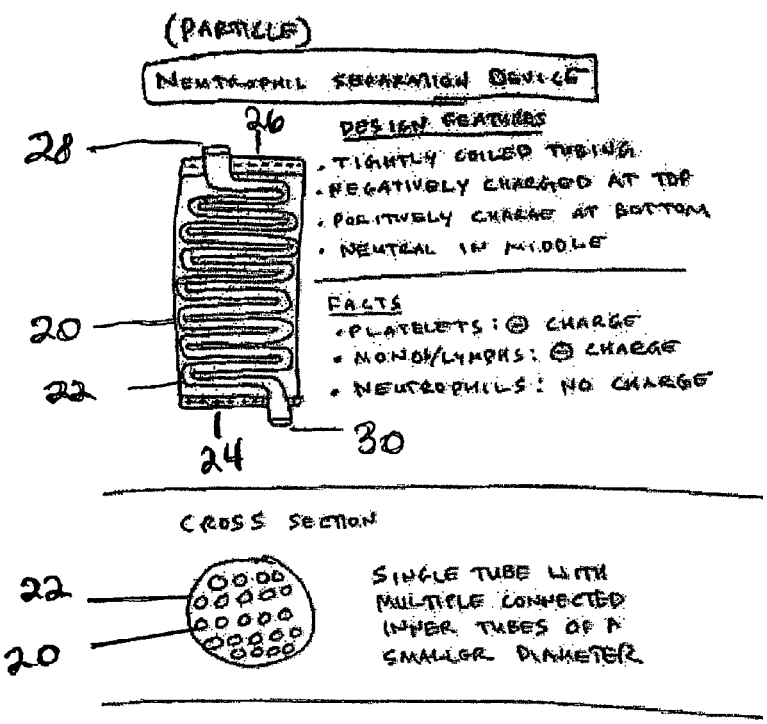
FIG. 3 shows another embodiment of the separation device of the invention.
FIG. 4 shows the embodiment of FIG. 3 in cross section view.

Another embodiment of a cell separation device of the invention is shown in FIG. 3. The coiled tubing 20 is packed into a unit 22 which is positively charged at the bottom 24 and negatively charged at the top 26. The fluid to be separated enters from the top 28 and exits through the bottom 30. FIG. 4 shows the same unit in cross section with the tubing 20 within the unit 22.

The tubing may be made of any appropriate material including metal, non-metal, polymer or plastic, elastomer, or biologically derived material. Preferred metals include but are not limited to stainless steel, aluminum, nitinol, cobalt, chrome, and titanium. Polymer materials include but are not limited to polyacetal, polyurethane, polyester, polytetrafluoroethylene, polyethylene, polymethylmethacrylate, polyhydroxyethyl methacrylate, polyvinyl alcohol, polypropylene, polymethylpentene, polyetherketone, polyphenylene oxide, polyvinyl chloride, polycarbonate, polysulfone, acrylonitrile-butadiene-styrene polyetherimide, polyvinylidene fluoride, and copolymers and combinations thereof. Other preferred materials include polysiloxane, fluorinated polysiloxane, ethylene-propylene rubber, fluoroelastomer and combinations thereof. Other preferred materials include polylactic acid, polyglycolic acid, polycaprolactone, polyparadioxanone, polytrimethylene carbonate and their copolymers. Preferably, the tubing is made of medical grade plastic or silicon.

The outer unit may be made of any appropriate material including metal, non-metal, polymer or plastic, elastomer, or biologically derived material. Preferred metals include but are not limited to stainless steel, aluminum, nitinol, cobalt chrome, and titanium. Non-metals include but are not limited to glass, silica, and ceramic. Polymer materials include but are not limited to polyacetal, polyurethane, polyester, polytetrafluoroethylene, polyethylene, polymethylmethacrylate, polyhydroxyethyl methacrylate; polyvinyl alcohol, polypropylene, polymethylpentene, polyetherketone, polyphenylene oxide, polyvinyl chloride, polycarbonate, polysulfone, acrylonitrile-butadiene-styrene, polyetherimide, polyvinylidene fluoride, and copolymers and combinations thereof. Other preferred materials include polysiloxane, fluorinated polysiloxane, ethylene-propylene rubber, fluoroelastomer and combinations thereof. Other preferred materials include polylactic acid, polyglycolic acid, polycaprolactone, polyparadioxanone, polytrimethylene carbonate and their copolymers, collagen, elastin, chitin, coral, hyaluronic acid, and bone.

The charge may be applied by any conventional device for applying a charge such as a battery, a direct electric current or a magnetic field.

The fluid input may be attached by any means including needle or tubing which may be any of the materials described above. Connection may be made to a bag, bottle or syringe containing an aqueous sample such as blood or platelet rich plasma.

In a preferred embodiment, the tubing diameter is about 10-100 microns. Preferably, the tubing would be 10-50 microns in diameter and most preferably about 15 to 20 micron diameter.

The length of the tubing varies from 1-100 cm as a function of the volume of the bodily fluid. For example, for small volumes the length may be 1-5 cm. For larger volumes the length may be 50-100 cm. For intermediate volumes, the length may be 5-50 cm. In some cases, tubing longer than 100 cm is appropriate.

In one embodiment, the device described above is part of a larger system such as a system for concentrating platelets or other blood processing device.

In a preferred embodiment, the device in one embodiment is used to remove neutrophils from platelet rich plasma. Preferably, the device is used in combination with a means to obtain the platelet rich plasma from plasma. Platelet rich plasma may be obtained by well known means. One such protocol is Smart PReP® provided Harvest and is shown in Appendix 2. Other systems for isolation of platelet rich plasma include Medtronic Magellan®, the GPS® System from Biomet Merck and Symphony® PCS from DePuy (See Appendices 3-5) or any device capable of producing platelet rich plasma.

Also, encompassed are compositions produced by the device including platelet rich plasma or whole blood which has been depleted of white blood cells, particularly neutrophils. In a preferred embodiment, the neutrophils have been depleted by at least 5%, in a more preferred embodiment, the neutrophils are depleted by at least 10%, in a more preferred embodiment, the neutrophils are depleted by at least 15%, in a more preferred embodiment, the neutrophils are depleted by at least 20%, in a more preferred embodiment, the neutrophils are depleted by at least 25%, in a more preferred embodiment, the neutrophils are depleted by at least 30%, in a more preferred embodiment, the neutrophils are depleted by at least 35%, in a more preferred embodiment, the neutrophils are depleted by at least 40%, in a more preferred embodiment, the neutrophils are depleted by at least 45%, in a more preferred embodiment, the neutrophils are depleted by at least 50%, in a more preferred embodiment, the neutrophils are depleted by at least 55%, in a more preferred embodiment, the neutrophils are depleted by at least 60%, in a more preferred embodiment, the neutrophils are depleted by at least 65%, in a more preferred embodiment, the neutrophils are depleted by at least 70%, in a more preferred embodiment, the neutrophils are depleted by at least 75%. In a most preferred embodiment, the neutrophils in the platelet rich plasma or whole blood are depleted by more than 75%.

The neutrophil-depleted platelet-rich plasma or neutrophil-depleted whole blood compositions are useful for the treatment of several types of tissue damage or injury. As used herein, the term "injury" is a broad term and is used in the ordinary sense to refer, without limitation, to any tissue damage including a wound, trauma or lesion or any tissue degeneration. In particular, the neutrophil-depleted platelet-rich plasma or neutrophil-depleted whole blood compositions may be used to treat incomplete repair of various connective tissues.

Embodiments of the invention are directed to a method of treating incomplete repair in a patient's connective tissue comprising: obtaining a neutrophil-depleted platelet-rich plasma or neutrophil-depleted whole blood composition; determining a lesion that comprises the incomplete repair in the patient's connective tissue; and minimally invasively introducing the neutrophil-depleted platelet-rich plasma or neutrophil-depleted whole blood composition into and around the lesion. In one embodiment, the invention relates to the method wherein the neutrophil-depleted platelet-rich plasma or neutrophil- depleted whole blood composition is at or above physiological pH. In one embodiment, the invention relates to the method wherein the neutrophil-depleted platelet-rich plasma or neutrophil-depleted whole blood composition optionally includes platelet releasate. In an embodiment, the invention relates to the method further comprising: mixing into the neutrophil-depleted platelet-rich plasma or neutrophil-depleted whole blood composition one or more of the ingredients selected from thrombin, epinephrine, collagen, calcium salts, and pH adjusting agents. Also useful are materials to promote degranulation or preserve platelets, additional growth factors or growth factor inhibitors, small molecule pharmaceuticals such as NSAIDS, steroids, and anti-infective agents. In an embodiment, the invention relates to the method wherein the patient's connective tissue is selected from: tendons, ligaments, joint capsules, and fascial tissues. In an embodiment, the invention relates to the method with the proviso that the neutrophil-depleted platelet-rich plasma or neutrophil-depleted whole blood composition is substantially free from exogenous activators prior to its introduction into and around the region of the incomplete repair in the patient's connective tissue. In an embodiment, the invention relates to the method wherein the neutrophil-depleted platelet-rich plasma or neutrophil-depleted whole blood composition comprises is obtained from the patient.

The invention further relates to a method of treating incomplete repair in a patient's connective tissue comprising: obtaining a neutrophil-depleted platelet-rich plasma or neutrophil-depleted whole blood composition; determining a lesion that comprises the incomplete repair in the patient's connective tissue; and introducing the neutrophil-depleted platelet-rich plasma or neutrophil-depleted whole blood composition into and around the lesion, with the proviso that substantially no activator is added to the neutrophil-depleted platelet-rich plasma or neutrophil-depleted whole blood composition prior to its introduction into and around the lesion. The invention also relates to the method wherein the neutrophil-depleted platelet-rich plasma or neutrophil-depleted whole blood composition is minimally invasively introduced into and around the lesion. The invention also relates to the method further comprising: mixing into the neutrophil-depleted platelet-rich plasma or neutrophil-depleted whole blood composition substantially simultaneously with its minimally invasive introduction into and around the lesion one or more of the ingredients selected from thrombin, epinephrine, collagen, calcium salts, and pH adjusting agents. Also useful are materials to promote degranulation or preserve platelets, additional growth factors or growth factor inhibitors, small molecule pharmaceuticals such as NSAIDS, steroids, and anti-infective agents. The invention also relates to the method wherein the patient's connective tissue is selected from: tendons, ligaments, joint capsules, and fascial tissues. The invention also relates to the method wherein introducing the neutrophil-depleted platelet-rich plasma or neutrophil-depleted whole blood composition into and around the lesion comprises activating platelets in the neutrophil-depleted platelet-rich plasma or neutrophil-depleted whole blood composition through the action of collagen present in the patient's connective tissue. The invention also relates to the method wherein the neutrophil-depleted platelet-rich plasma or neutrophil-depleted whole blood composition is at or above physiological pH. The invention also relates to the method wherein the neutrophil-depleted platelet-rich plasma or neutrophil-depleted whole blood composition comprises is obtained from the patient.

In a further embodiment, the invention relates to a method of treating lesions resulting from acute injury to or chronic disorders of the Medial Collateral Ligament of the knee or elbow, Extensor Carpi Radialis Brevis tendon, Anterior Talofibular Ligament at the ankle, Achilles tendon, posterior tibial tendon, patellar tendon, quadriceps tendon, Anterior Cruciate Ligament, Posterior Cruciate Ligament, spinal ligaments, disc materials, rotator cuff tendon, or biceps tendons comprising: obtaining a neutrophil-depleted platelet-rich plasma or neutrophil-depleted whole blood composition; determining a location of the lesion; and introducing the neutrophil-depleted platelet-rich plasma or neutrophil-depleted whole blood composition into and around the lesion, with the proviso that substantially no activator is added to the neutrophil-depleted platelet-rich plasma or neutrophil-depleted whole blood composition prior to its introduction into and around the lesion. In an embodiment, the invention relates to the method wherein the neutrophil-depleted platelet-rich plasma or neutrophil-depleted whole blood composition is minimally invasively introduced into and around the lesion. In an embodiment, the invention relates to the method further comprising: mixing into the neutrophil-depleted platelet-rich plasma or neutrophil-depleted whole blood composition substantially simultaneously with its minimally invasive introduction into and around the lesion one or more of the ingredients selected from thrombin, epinephrine, collagen, calcium salts, pH adjusting agents. Also useful are materials to promote degranulation or preserve platelets, additional growth factors or growth factor inhibitors, small molecule pharmaceuticals such as NSAIDS, steroids, and anti-infective agents. In an embodiment, the invention relates to the method wherein the neutrophil-depleted platelet-rich plasma or neutrophil-depleted whole blood composition is at or above physiological pH. In an embodiment, the invention relates to the method wherein source of the neutrophil-depleted platelet-rich plasma or neutrophil-depleted whole blood composition is from the patient.

In a further embodiment, the invention relates to a method of treating lesions resulting from injury or chronic disorders of cardiac muscle, skeletal muscle, organ systems, vascular tissue, disc material, spinal bodies, spinal cord, and brain tissue comprising: obtaining a neutrophil-depleted platelet-rich plasma or neutrophil-depleted whole blood composition; determining a lesion in need of treatment; and minimally invasively introducing the neutrophil-depleted platelet-rich plasma or neutrophil-depleted whole blood composition into and around the lesion. In an embodiment, the invention relates to the method wherein the neutrophil-depleted platelet-rich plasma or neutrophil-depleted whole blood composition optionally includes platelet releasate. In an embodiment, the invention relates to the method further comprising: mixing into the neutrophil-depleted platelet-rich plasma or neutrophil-depleted whole blood composition one or more of the ingredients selected from thrombin, epinephrine, collagen, calcium salts, and pH adjusting agents. Also useful are materials to promote degranulation or preserve platelets, additional growth factors or growth factor inhibitors, small molecule pharmaceuticals such as NSAIDS, steroids, and anti-infective agents. In an embodiment, the invention relates to the method wherein the neutrophil-depleted platelet-rich plasma or neutrophil-depleted whole blood composition is at or above physiological pH. In an embodiment, the invention relates to the method wherein the platelet composition comprises platelets obtained from the patient.

In an embodiment, the invention relates to the method wherein the patient's connective tissue is selected from: tendons, ligaments, joint capsules, and fascial tissues. In an embodiment, the invention relates to the method with the proviso that the neutrophil-depleted platelet-rich plasma or neutrophil-depleted whole blood composition is substantially free from exogenous activators prior to its introduction into and around the region of the incomplete repair in the patient' damaged or injured tissue. In an embodiment, the invention relates to the method wherein the neutrophil-depleted platelet-rich plasma or neutrophil-depleted whole blood composition is obtained from the patient.

The neutrophil-depleted platelet-rich plasma or neutrophil-depleted whole blood composition may be a biocompatible composition that comprises unactivated platelets, activated platelets, platelet releasate(s), or the like. In an embodiment, the inventive platelet composition comprises neutrophil-depleted platelet-rich plasma.

The term "platelet-rich plasma" or "PRP" as used herein is a broad term which is used in its ordinary sense and is a concentration of platelets greater than the peripheral blood concentration suspended in a solution of plasma, or other excipient suitable for administration to a human or non-human animal including, but not limited to isotonic sodium chloride solution, physiological saline, normal saline, dextrose 5% in water, dextrose 10% in water, Ringer solution, lactated Ringer solution, Ringer lactate, Ringer lactate solution, and the like. Typically, platelet counts range from 500,000 to 1,200,000 per cubic millimeter, or even more. PRP is formed from the concentration of platelets from whole blood, and may be obtained using autologous, allogenic, or pooled sources of platelets and/or plasma. PRP may be formed from a variety of animal sources, including human sources. In preferred embodiments, PRP according to the invention is buffered to physiological pH.

Platelets are cytoplasmic portions of marrow megakaryocytes. They have no nucleus for replication; the expected lifetime of a platelet is some five to nine days. Platelets are involved in the hemostatic process and release several initiators of the coagulation cascade. Platelets also release cytokines involved with initiating wound healing. The cytokines are stored in alpha granules in platelets. In response to platelet to platelet aggregation or platelet to connective tissue contact, as would be expected in injury or surgery, the cell membrane of the platelet is "activated" to secrete the contents of the alpha granules. The alpha granules release cytokines via active secretion through the platelet cell membrane as histones and carbohydrate side chains are added to the protein backbone to form the complete cytokine. Platelet disruption or fragmentation, therefore, does not result in release of the complete cytokine.

A wide variety of cytokines are released by activated platelets. Platelet derived growth factor (PDGF), transforming growth factor-beta (TGF-b), platelet-derived angiogenesis factor (PDAF) and platelet derived endothelial cell growth factor (PD-ECGF) and insulin-like growth factor (IGF) are among the cytokines released by degranulating platelets. These cytokines serve a number of different functions in the healing process, including helping to stimulate cell division at an injury site. They also work as powerful chemotactic factors for mesenchymal cells, monocytes and fibroblasts, among others. For the purposes of this patent, the term "releasate" refers to the internal contents of the platelet, including cytokines, which have the potential to affect another cells' function.

Historically, PRP has been used to form a fibrin tissue adhesive through activation of the PRP using thrombin and calcium, as disclosed in U.S. Pat. No. 5,165,938 to Knighton, and U.S. Pat. No. 5,599,558 to Gordinier et al., incorporated in their entirety by reference herein. Activation results in release of the various cytokines and also creates a clotting reaction within various constituents of the plasma fraction. The clotting reaction rapidly forms a platelet gel (PG) which can be applied to various wound surfaces for purposes of hemostasis, sealing, and adhesion.

In another embodiment, the neutrophil-depleted platelet-rich plasma or neutrophil-depleted whole blood composition may comprise releasate from platelets. The releasate comprises the various cytokines released by degranulating platelets upon activation. Many activators of platelets exist; these include calcium ions, thrombin, collagen, epinephrine, and adenosine diphosphate. Releasates according to the invention may be prepared according to conventional methods, including those methods described in U.S. Pat. No. 5,165,938 to Knighton, and U.S. Pat. No. 5,599,558 to Gordinier et al.

One disadvantage of conventional releasate strategies associated with the use of PRP as PG is the use of thrombin as a preferred activator. In particular, much thrombin used in PG is bovine thrombin, which can create problems due to contamination issues regarding Creutzfeldt-Jakob disease. Many bovine materials are suspect due to possible prion contamination, and so use of bovine thrombin is disfavored in surgery. Human pooled thrombin is likewise disfavored due to the potential of contamination with various materials such as viruses, prions, bacteria and the like. Recombinant human thrombin might also be used, but is quite expensive.

It is a particular advantage of the present invention that exogenous or extra activators need not be administered to a patient. Collagen, a major component of connective tissues, is a strong activator of platelets. Thus, when the inventive platelet composition is introduced into and/or around connective tissue, platelets in the platelet composition may bind to the collagen and then be activated. This reduces or eliminates the need for administering an exogenous activator such as thrombin. The disadvantages of thrombin use have been noted above. Other strong activators, such as calcium ions, can cause severe pain, unintentional clotting, and other undesirable side effects. Thus, in an embodiment of the invention, no or substantially no exogenous activator is present or added as part of the neutrophil-depleted platelet-rich plasma or neutrophil-depleted whole blood composition, or is used in the preparation of the neutrophil-depleted platelet-rich plasma or neutrophil-depleted whole blood composition. Of course, exogenous activators may still be employed if a physician determines that they are medically necessary or desirable.

The platelet composition may be prepared using any conventional method of isolating platelets from whole blood or platelet-containing blood fractions. These include centrifugal methods, filtration, affinity columns, and the like. If the platelet composition comprises PRP, then conventional methods of obtaining PRP, such as those disclosed in U.S. Pat. No. 5,585,007 and U.S. Pat. No. 5,788,662 both to Antanavich et al., incorporated herein by reference in their entirety, may be utilized.

The neutrophil-depleted platelet-rich plasma or neutrophil-depleted whole blood composition may be delivered to an individual in need thereof by convention means which include injection using a syringe or catheter. The neutrophil-depleted platelet-rich plasma or neutrophil-depleted whole blood composition may also be delivered via a dermal patch, a spray device or in combination with an ointment, bone graft or drug. It may further be used as a coating on suture, stents, screws, plates or some other implantable medical device. Finally, it may be used in conjunction with a bioresorbable drug or device.

The site of delivery of the neutrophil-depleted platelet-rich plasma or neutrophil-depleted whole blood composition is at or near the site of tissue injury and/or damage. The site of tissue injury or damage is determined by well-established methods including imaging studies and patient feedback or a combination thereof. The preferred imaging study used is determined by the tissue type. Commonly used imaging methods include, but are not limited to MRI, X-ray, CT scan, Positron Emission tomography (PET), Single Photon Emission Computed Tomography (SPECT), Electrical Impedance Tomography (EIT), Electrical Source Imaging (ESI), Magnetic Source Imaging (MSI), laser optical imaging and ultrasound techniques. The patient may also assist in locating the site of tissue injury or damage by pointing out areas of particular pain and/or discomfort.

Adjusting the pH of platelet compositions has been used to prolong the storage time of unactivated platelets, as disclosed in U.S. Pat. No. 5,147,776 to Koerner, Jr. and U.S. Pat. No. 5,474,891 to Murphy, incorporated by reference herein. pH may be adjusted using a variety of pH adjusting agents, which are preferably physiologically tolerated buffers, but may also include other agents that modify pH including agents that modify lactic acid production by stored platelets. Especially useful are those pH adjusting agents that result in the pH of the platelet composition becoming greater than or equal to physiological pH. In an embodiment, the pH adjustment agent comprises sodium bicarbonate , Physiological pH, for the purposes of this invention, may be defined as being a pH ranging from about 7.35 to about 7.45. pH adjusting agents useful in the practice of this invention include bicarbonate buffers (such as sodium bicarbonate), calcium gluconate, choline chloride, dextrose (d-glucose), ethylenebis(oxyethylenenitrilo)tetraacetic acid (EGTA), 4-(2-hydroxyethyl)-1-piperazineethanesulfonic acid (HEPES), maleic acid, 4-morpholinepropanesulfonic acid (MOPS), 1,4-piperazinebis (ethanesulfonic acid) (PIPES), sucrose, N-tris (hydroxymethyl)methyl-2-aminoethanesulfonic acid (TES), tris(hydroxymethyl)aminomethane (TRIS BASE), tris(hydroxymethyl)aminomethane hydrochloride (TRIS.HCl), and urea. In a preferable embodiment, the pH adjusting agent is a bicarbonate buffer, more preferably, sodium bicarbonate.

For the purposes of this patent, the term "tissues" includes but is not limited to cardiac and skeletal muscle, disc material, vertebral bodies, internal organs, brain and spinal cord tissue, vascular tissue such as arteries and veins and non-differentiated tissue.

For the purposes of this patent, connective tissues comprise tendons, ligaments, fascial tissues, and joint capsules. In a preferable embodiment, connective tissues comprise the Medial Collateral Ligament of the knee or elbow, Extensor Carpi Radialis Brevis tendon (tennis elbow), Anterior Talofibular Ligament at the ankle, Achilles tendon, Anterior Cruciate Ligament, Posterior Cruciate Ligament, posterior tibial tendon, patellar tendon, quadriceps tendon, rotator cuff tendon, and biceps tendons.

Incomplete repair, as it is used in the context of this patent application, may be defined to mean repair that is disorganized, substantially non-existent (such as in the case of an unhealed tear), or otherwise pathological. Disorganized repair is characterized by a disorganized angiofibroblastic dysplasia, with degenerative, immature and avascular tissue. Such tissue is weaker than normal connective tissue and lacks the strength to function normally. This tissue also limits the patient by causing pain and negatively impacting the patient's quality of life. Substantially non-existent repair might occur in a situation where a connective tissue is torn and does not heal properly subsequently to the tear. Otherwise pathological repair may be any other type of repair in which the tissue is not repaired to be substantially the same as the tissue was before tissue repair was necessary.

It will be apparent to those skilled in the art that various modifications and variations can be made to the present invention without departing from the spirit or scope of the invention. Thus, it is intended that the present invention cover the modifications and variations of the present invention provided that they come within the scope of the appended claims and their equivalents. The following examples are illustrative of the present invention, and are not intended to limit it.

EXAMPLE 1

Figure 5:
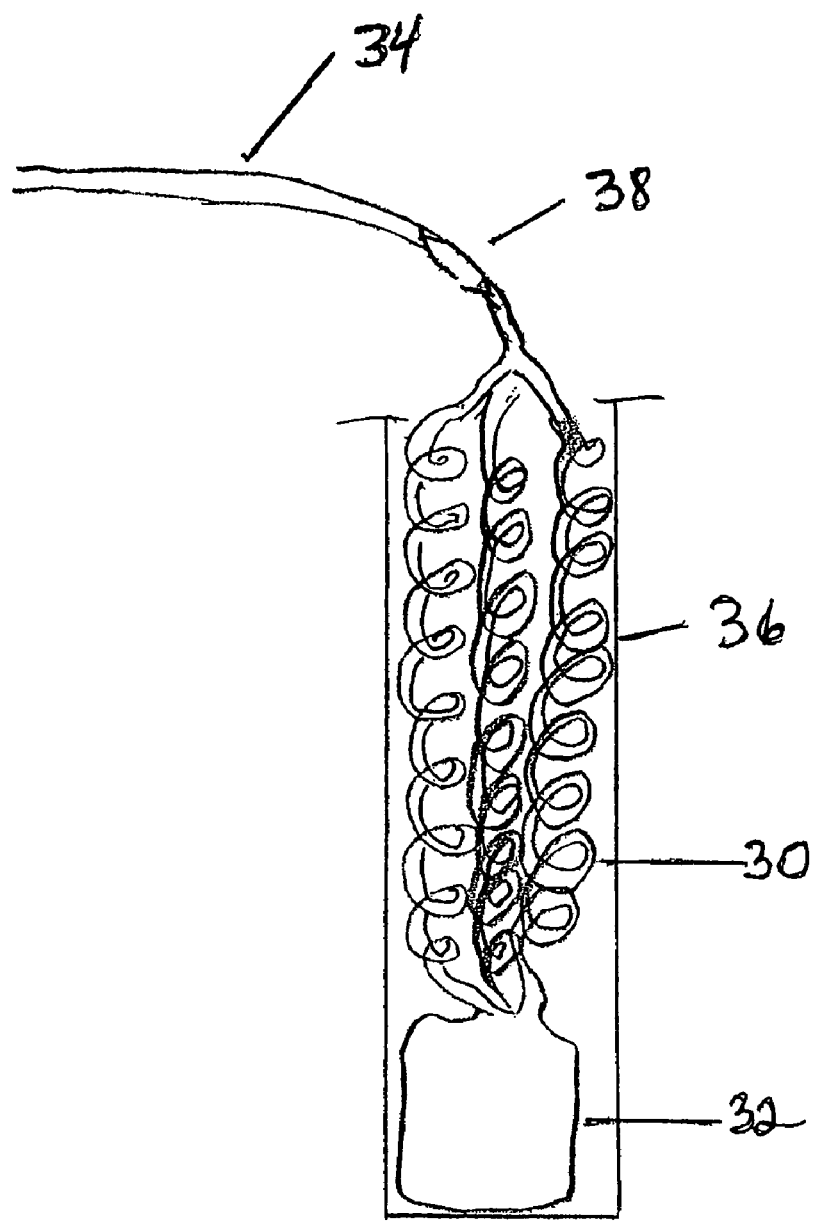
FIG. 5 shows another embodiment of the separation device of the invention.

FIG. 5 shows a series of coiled tubes 30 for separation of the cellular components as described above. The tubes empty into a collection chamber 32. The sample to be purified enters through tubing 34 which may connect to the separation device 36 by a tubing adaptor 38. When a sample of platelet rich plasma enters the device, the smaller platelets are able to travel through the coiled tubing 30 to the collection chamber 32 more quickly than the neutrophils because of their smaller size and greater deformability. The neutrophils are retained in the coiled tubing.

EXAMPLE 2

Figure 6:
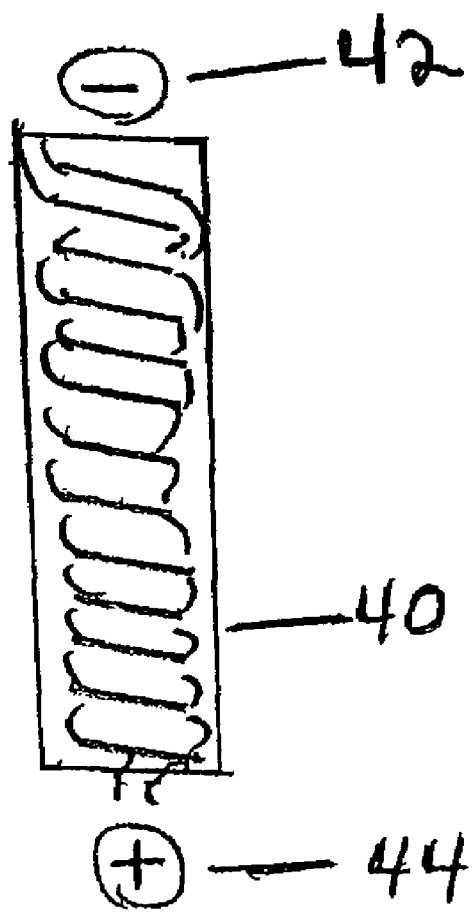
FIG. 6 shows another embodiment of the separation device of the invention.

In an alternative design, the device could exist within an electrical field as shown in FIG. 6. For example, each of the coiled tubes shown in Example 1 above, could be encased within a chamber 40 that has a negative charge at its apex 42 and a positive charge at it base 44. The center of the chamber would be neutral in charge. When the sample enters the chamber, the platelets are able to travel through the coiled tubing as in Example 1 because of their small size and deformability. Additionally, as the platelets carry a net negative charge, their separation is further facilitated because of the positive charge at the bottom of the chamber.

EXAMPLE 3

Figure 7:
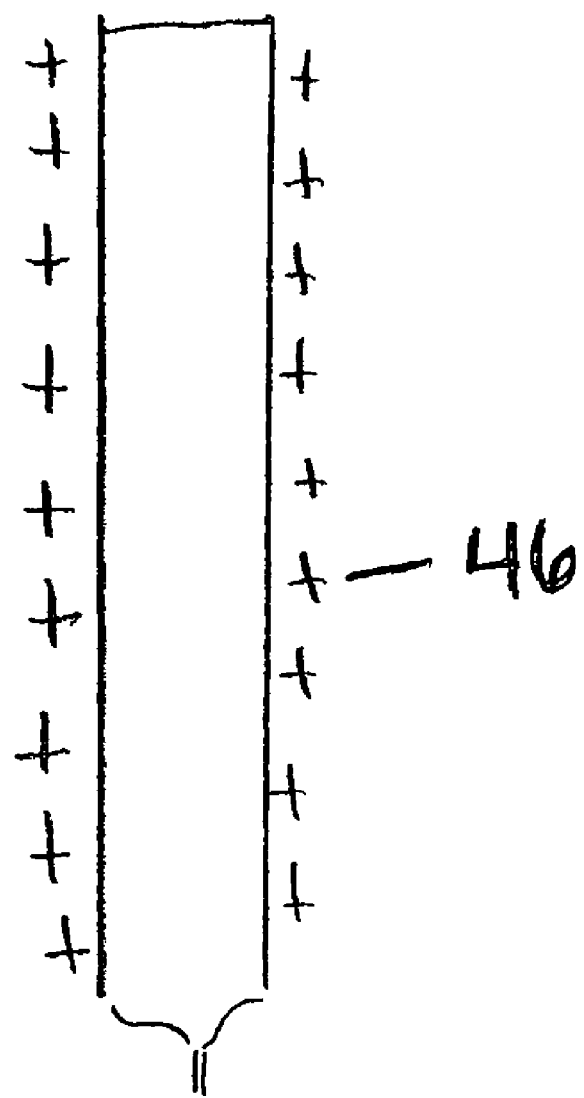
FIG. 7 shows another embodiment of the separation device of the invention.

In another alternative design, the device could be made of tubing that conducts electricity (FIG. 7). A charge 46 could then be run through the tubing and a gradient could be established. In the device shown in FIG. 7, the negatively charged blood components such as the platelets would be hindered by the positive charge of the walls of the tubing. In this example, the neutrophils would be collected first and separated from the other blood components. As in Example 2 above, the separation of the neutrophils from the platelets is based upon the small size, deformability and negative charge of the platelets relative to the neutrophils.

EXAMPLE 4

Figure 8:
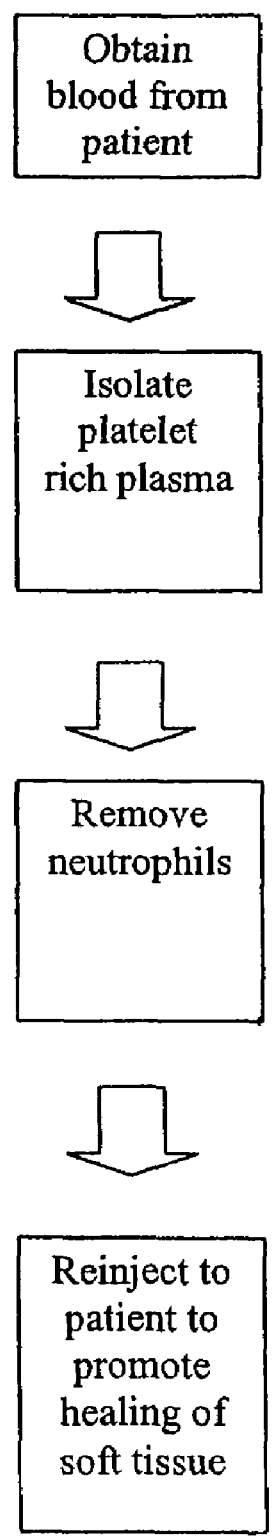
FIG. 8 shows a method of using the separation device of the invention in a method to promote healing of soft tissue.

FIG. 8 illustrates how the process described in Examples 1-3 above may be coupled to a device for isolation of platelet rich plasma, preferably using the patients own blood as a source. The platelets are enriched followed by removal of the neutrophils. In an alternate embodiment, the neutrophils could be removed before isolation of the platelets. Thus, the device described herein is incorporated into an existing device that produces platelet rich plasma or filters blood in some other manner. Finally, the resulting product of filtration—platelet rich plasma that has been depleted of neutrophils—is used in a therapeutic manner to initiate, enhance or accelerate healing in a body tissue.

EXAMPLE 5

PRP was prepared using a centrifuge unit made by Harvest (Plymouth, Mass.). (Similar units are available as The Biomet GPS system, the Depuy Symphony machine and the Medtronic Magellan machine.) Approximately 55 cc of blood was drawn from the patient using a standard sterile syringe, combined with 5 cc of a citrate dextrose solution for anticoagulation, and then spun down to isolate the platelets according to the manufacturer's protocol. These platelets were then resuspended in approximately 3 cc of plasma. The resulting platelet rich plasma solution (PRP) was quite acidic and was neutralized with using approximately 0.05 cc of an 8.4% sodium bicarbonate buffer per cc of PRP under sterile conditions to approximately physiologic pH of 7.4. The PRP was not activated through addition of exogenous activators. Neutrophils were removed from the PRP composition by any of the methods described above.

EXAMPLE 6

Fifty cc of whole blood is drawn from a patient, and then prepared according to the method of Knighton, U.S. Pat. No. 5,165,938, column 3. The PRP is activated according to Knighton using recombinant human thrombin. The degranulated platelets are spun down and the releasate containing supernatant is recovered. Neutrophils were removed from the PRP composition by any of the methods described above. The neutrophil-depleted releasate may be optionally pH adjusted to a pH of 7.4 using sodium bicarbonate buffer.

EXAMPLE 7

Thirty ml of whole blood were drawn from a patient. A platelet composition was prepared according to Example 1 of U.S. Pat. No. 5,510,102 to Cochrum, incorporated herein by reference in its entirety, except that no alginate is added to the platelet composition. Neutrophils were removed from the PRP composition by any of the methods described above to obtain neutrophil-depleted PRP.

EXAMPLE 8

Neutrophil-depleted PRP is administered to patients presenting with lateral epicondylitis (tennis elbow). The patients are evaluated to obtain a visual pain score, a Mayo Elbow Score, and grip strength. For the visual analog pain score, zero equals "no pain" and 100 equals "the worst pain possible." The Mayo elbow score is an overall function score with a higher score indicating better overall function. The values of the two scores are statistically evaluated using a paired sample T test with significance set at $p<0.05$.

Each patient is then given 5 mg of Valium p.o. 30 minutes prior to the inventive tendon procedure. Patients are then prepped and draped in a sterile manner. A local anesthetic of 0.5% bupivicaine with epinephrine is infiltrated into the skin, subcutaneous structures and extensor carpi radialis brevis tendon. Care is taken to keep the local anesthetic out of the elbow joint.

Two to three minutes after administration of the local anesthetic, approximately 3-5 cc of the neutrophil-depleted PRP of Example 5 is introduced into the extensor carpi radialis brevis tendon at the elbow via a 22 gauge needle. The control group receive a numbing shot (Bupivicaine). Multiple punctures into the tendon approximately 0.5-1 cm from its origin are made. Promptly after the minimally invasive introduction of either the neutrophil-depleted PRP of Example 5 or the numbing shot, the patient's arm is immobilized at about 90% of flexion without elevation of the arm or hand. The surgical area is then sterilely dressed and the patient is asked not to move their arm for 30 minutes. Each patients' neurovascular, pain and function status is evaluated shortly after the injection, and at 30 minutes following the end of the procedure. Each patient is given oral narcotic pain medication as needed for the first 24-48 hours after the procedure. A formal postoperative stretching and strengthening program may be initiated at 2-3 days after the procedure. The visual pain score, Mayo Elbow Score, and grip strength are all monitored post-procedure.

EXAMPLE 9

A patient presenting with Achilles tendinosis is given 5 mg of Valium p.o. 30 minutes prior to the inventive tendon procedure. The patient is then prepped and draped in a sterile manner. A local anesthetic of 0.5% bupivicaine with epinephrine is infiltrated into the skin, subcutaneous structures and Achilles tendon. Care is taken to keep the local anesthetic out of the ankle joint.

Two to three minutes after administration of the local anesthetic, approximately 3-5 cc of the neutrophil-depleted PRP composition of Example 5 is introduced into the Achilles tendon just above the ankle via a 22 gauge needle. Multiple punctures into the tendon approximately 0.5-1 cm from its insertion are made. Promptly after the minimally invasive introduction of the neutrophil-depleted PRP composition of Example 5, the patient's lower leg and foot are immobilized without elevation of the leg. The surgical area is then sterilely dressed and the patient is asked not to move their leg for 30 minutes. The patient's neurovascular, pain and function status is evaluated shortly after the injection, and at 30 minutes following the end of the procedure. The patient is given oral narcotic pain medication as needed for the first 24-48 hours after the procedure. The Achilles tendon remains immobilized for one week following the procedure, followed by a formal postoperative stretching and strengthening program initiated at 8-10 days after the procedure.

EXAMPLE 10

A patient presenting with a medial collateral ligament tear of the elbow is given 5 mg of Valium p.o. 30 minutes prior to the inventive tendon procedure. The patient is then prepped and draped in a sterile manner. A local anesthetic of 0.5% bupivicaine with epinephrine is infiltrated into the skin, subcutaneous structures and medial collateral ligament at the elbow. Care is taken to keep the local anesthetic out of the elbow joint.

Two to three minutes after administration of the local anesthetic, approximately 3-5 cc of the neutrophil-depleted PRP composition of Example 5 is introduced into the medial collateral ligament at the elbow via a 22 gauge needle. Multiple punctures into the ligament approximately 0.5-1 cm from its origin are made. Promptly after the minimally invasive introduction of the neutrophil-depleted PRP composition of Example 5, the patient's elbow and arm are immobilized at about 90% of flexion without elevation of the arm or hand. The surgical area is then sterilely dressed and the patient is asked not to move their arm for 30 minutes. The patient's neurovascular, pain and function status is evaluated shortly after the injection, and at 30 minutes following the end of the procedure. The patient is given oral narcotic pain medication as needed for the first 24-48 hours after the procedure. An optional formal post-operative stretching and strengthening program may be initiated at 2-3 days after the procedure.

EXAMPLE 11

Cardiac Muscle

A patient presents with either an acute (i.e. heart attack) or chronic dysfunction (i.e. congestive heart failure) of cardiac muscle. An neutrophil-depleted PRP composition is prepared as described in Example 5 Approximately 0.05 cc of an 8.4% sodium bicarbonate buffer per cc of extract is used to raise the pH to or slightly above 7.4. The extract is not activated through the addition of exogenous agent(s).

The neutrophil-depleted PRP composition is then introduced into the area of dysfunctional cardiac muscle via a catheter. The neutrophil-depleted PRP composition may also be combined with an implantable device such as a stent.

EXAMPLE 12

Skeletal Muscle

A patient presents with weakness or atrophy of skeletal muscle. This could be the result of an injury or after a surgical procedure. Using the technique of Example 5, a neutrophil-depleted PRP composition is obtained and buffered to physiologic pH.

The area of weakness or atrophy is identified and then after using 0.5% bupivicaine with epinephrine as a local anesthetic, the neutrophil-depleted PRP composition is introduced into the muscle via a 22 g needle. This can be done a single time or it may require multiple injections. Postoperatively, the patient is started on a site specific stretching and strengthening protocol.

EXAMPLE 13

Disc Material/Vertebral Bodies

A patient presents with low back pain and either bulging or black discs on an MRI scan. Using the technique of Example 5, a neutrophil-depleted PRP composition is obtained and buffered to physiologic pH.

The disc in question is identified by X-ray guidance and then the neutrophil-depleted PRP composition is introduced into the disc space via small gauge catheter. This procedure could be done alone or in combination with a thermal/radiofrequency ablation procedure. The neutrophil-depleted PRP composition could also be injected into a vertebral body that has sustained a compression fracture with or without the use of a balloon prior to injection.

EXAMPLE 14

Pancreas/Any Internal Organ

A patient presents with diabetes and poor insulin production. Using the technique of Example 5, a neutrophil-depleted PRP composition is obtained and buffered to physiologic pH.

Under CT guidance and conscious sedation, the neutrophil-depleted PRP composition is introduced via a small gauge catheter into the pancreas. The neutrophil-depleted PRP composition is then injected into the islet cells to stimulate repair of these cells and thus restore insulin production.

EXAMPLE 15

Brain/Spinal Cord

A patient presents with an acute neurologic deficit such as a spinal cord injury or stroke. Using the technique of Example 5, a neutrophil-depleted PRP composition is obtained and buffered to physiologic pH.

Under MRI guidance and conscious sedation, the neutrophil-depleted PRP composition is introduced into the area of injury or deficit. The neutrophil-depleted PRP composition initiates or assists with repair of the locally damaged cells.

EXAMPLE 16

Vascular Tissue

A patient presents with an area of hypovascularity in his or her lower extremities. The patient has a diagnosis of peripheral vascular occlusive disease. Using the technique of Example 5, a neutrophil-depleted PRP composition is obtained and buffered to physiologic pH.

The area of hypovascularity is blocked with bupivicaine and then the neutrophil-depleted PRP composition is introduced into either the muscle or soft tissue. The neutrophil-depleted PRP composition induces angiogenesis and new blood vessel formation.

EXAMPLE 17

Wound Healing

A patient presents with a chronic wound that is not healing properly. This could be a diabetic foot ulcer. Using the technique of Example 5, a neutrophil-depleted PRP composition is obtained and buffered to physiologic pH.

The wound is carefully cleansed and debrided as needed. The neutrophil-depleted PRP composition is then carefully injected into and around the chronic wound and its edges. It is held in place with an occlusive bandage or combined with an ointment. This process may be repeated as needed until the wound has healed.

EXAMPLE 18

Neoplastic Tissue

A patient presents with either a benign or malignant tumor or process. Using the technique of Example 5, a neutrophil-depleted PRP composition is obtained and buffered to physiologic pH. The neutrophil-depleted PRP composition can be used either in vivo or in vitro to initiate or induce tumor cell death.

Specifically, the neutrophil-depleted PRP composition is injected into a solid tumor with CT or MRI guidance via a small catheter. Alternatively, cancer cells after being grown in a media containing neutrophil-depleted PRP could be reintroduced back into the body to attack and kill the remaining tumor. Without intending to be limited by theory, it is hypothesized that the media containing neutrophil-depleted PRP has either the ability to cause tumor cell apoptosis (cell death) in vivo or it may have the ability to transform cancer cells into normal cells.

EXAMPLE 19

Infections

A patient presents with a superficial or deep infection. Using the technique of Example 5, a neutrophil-depleted PRP composition is obtained and buffered to physiologic pH.

The area of the infection is identified and the neutrophil-depleted PRP composition is then directly applied or percutaneously introduced. This could be done under local or general anesthesia and with or without imaging guidance.

EXAMPLE 20

Cell Cultures of Any Tissue

A researcher or clinician wishes to grow a cell culture of either fibroblasts or osteoarthritic cartilage cells. Using the technique of Example 5, a neutrophil-depleted PRP composition is obtained and buffered to physiologic pH.

The cells are then isolated and grown in a media rich in the neutrophil-depleted PRP composition in various conditions and dilutions. The neutrophil-depleted PRP composition promotes cell differentiation and production of proteins such as collagen. The neutrophil-depleted PRP composition may augment or promote the ability of the cells to transform into normal cells. Without intending to be limited by theory, it is hypothesized the neutrophil-depleted PRP composition may convert the osteoarthritic cartilage cells to a more functional cell line that is reinjected into a diseased or injured joint. Alternatively, the neutrophil-depleted PRP composition is directly introduced into an osteoarthritic joint to reverse the course of the disease. This is done under local anesthesia in a sterile manner.

Finally, the neutrophil-depleted PRP composition may be used to help grow and differentiate any tissue or cell line in vivo or in vitro.

Although the Examples above are described with regards to separation of neutrophils from platelet rich plasma, the separation device described above is not limited to this embodiment and may be used for separation of any kind of cell, protein or particle from an aqueous sample. While the described embodiment represents the preferred embodiment of the present invention, it is to be understood that modifications will occur to those skilled in the art without departing from the spirit of the invention. The scope of the invention is therefore to be determined solely by the appended claims.

What is claimed is:

1. A device for separation of neutrophils from platelet rich plasma comprising:
    an inlet end portion comprising an inlet port for receiving a sample of platelet rich plasma;
    an outlet end portion comprising at least one collection port for removing neutrophil-depleted platelet rich plasma; and
    a flow path placed within an electric field comprising a tubular material in fluid communication with the inlet port and the at least collection port;
wherein the tubular material is latticed or coiled, and has a diameter of 10-100 microns; and
wherein the outlet end has a positive charge and the inlet end has a negative electrical charge.

2. The cell separation device of claim 1, wherein the tubular material is made of plastic or silicon.

3. A blood filtering device that includes the cell separation device of claim 1.

4. A device for producing platelet rich plasma which includes the cell separation device of claim 1.

* * * * *

UNITED STATES PATENT AND TRADEMARK OFFICE
CERTIFICATE OF CORRECTION

PATENT NO. : 7,462,268 B2  
APPLICATION NO. : 11/205283  
DATED : December 9, 2008  
INVENTOR(S) : Allan Mishra Page 1 of 1

It is certified that error appears in the above-identified patent and that said Letters Patent is hereby corrected as shown below:

Column 1, Line 10, "BACK GROUND" should be changed to --BACKGROUND--

Column 3, Line 13, "of tissue injury, ." should be changed to --of tissue injury.--

Column 4, Lines 62-63, "acrylonitrile-butadiene-styrene" should be changed to

--acrylonitrile-butadiene-styrene,--

Column 10, Line 57, "sodium bicarbonate ," should be changed to --sodium bicarbonate.--

Column 18, Line 3, "at least collection" should be changed to --at least one collection--

Column 18, Line 4, "latticed or coiled," should be changed to --latticed or coiled--

Column 18, Line 6, "positive charge" should be changed to --positive electrical charge--

Column 18, Line 8, "The cell separation device" should be changed to --The device--

Column 18, Line 11, "includes the cell separation" should be changed to --includes the--

Column 18, Line 14, "the cell separation device" should be changed to --the device--

Signed and Sealed this

Twenty-eighth Day of April, 2009

JOHN DOLL  
*Acting Director of the United States Patent and Trademark Office*